United States Patent
Wang et al.

(10) Patent No.: US 10,617,356 B2
(45) Date of Patent: Apr. 14, 2020

(54) GARMENT AND CARDIAC DATA PROCESSING

(71) Applicants: Anhui Huami Information Technology Co., Ltd., Hefei, Anhui (CN); Huami Inc., Mountain View, CA (US)

(72) Inventors: Hui Wang, Anhui (CN); Yajun Zhao, Anhui (CN); Wang Huang, Hefei (CN); Yuanxiang Wang, Mountain View, CA (US); Yuchen Wang, Mountain View, CA (US); Fei Wang, Mountain View, CA (US)

(73) Assignees: Anhui Huami Information Technology Co., Ltd., Hefei, Anhui (CN); Huami Inc., Mountain View, CA (US)

( * ) Notice: Subject to any disclaimer, the term of this patent is extended or adjusted under 35 U.S.C. 154(b) by 171 days.

(21) Appl. No.: 15/677,671

(22) Filed: Aug. 15, 2017

(65) Prior Publication Data
US 2018/0007983 A1 Jan. 11, 2018

Related U.S. Application Data

(63) Continuation-in-part of application No. PCT/CN2017/075572, filed on Mar. 3, 2017, and a
(Continued)

(30) Foreign Application Priority Data

Mar. 15, 2016 (CN) .......................... 2016 1 0150885

(51) Int. Cl.
*A61B 5/0408* (2006.01)
*A61B 5/00* (2006.01)
(Continued)

(52) U.S. Cl.
CPC ........ *A61B 5/6805* (2013.01); *A41D 13/1281* (2013.01); *A61B 5/0428* (2013.01);
(Continued)

(58) Field of Classification Search
None
See application file for complete search history.

(56) References Cited

U.S. PATENT DOCUMENTS 3,534,727 A * 10/1970 Roman .............. A61B 5/04085
600/389
4,608,987 A * 9/1986 Mills .................... A61B 5/0408
600/389
(Continued)

FOREIGN PATENT DOCUMENTS

| CN | 1933776 A | 3/2007 |
|---|---|---|
| CN | 103126718 A | 6/2013 |

(Continued)

OTHER PUBLICATIONS

"Accelerometer Placement for Posture Recognition and Fall Detection", H. Gjoreskiet al, Intelligent Environment, 2011.
(Continued)

*Primary Examiner* — Kennedy Schaetzle
(74) *Attorney, Agent, or Firm* — Young Basile Hanlon & MacFarlane, P.C.

(57) ABSTRACT

A method for processing electrocardiograph (ECG) data using a garment includes determining, by a processor, a current working lead from ECG leads formed in advance using flexible electrodes in the garment based on a current ECG monitor type, and receiving, by the processor through lead wires corresponding to the current working lead, ECG data collected by flexible electrodes corresponding to the current working lead. A wearable apparatus for processing ECG data includes at least two flexible electrodes, in which
(Continued)

the at least two flexible electrodes are capable of forming different leads based on predetermined configurations, at least two lead wires, and an ECG data collector configured to receive ECG data collected by the at least two flexible electrodes, in which each of the at least two flexible electrodes connects to the ECG data collector via at least one of the at least two lead wires.

15 Claims, 9 Drawing Sheets

Related U.S. Application Data continuation-in-part of application No. 15/364,743, filed on Nov. 30, 2016, now Pat. No. 10,123,741.

(51) Int. Cl.
    A61B 5/0428    (2006.01)
    A41D 13/12     (2006.01)
    A61B 5/0464    (2006.01)
    A61B 5/0472    (2006.01)
    A61B 5/046     (2006.01)

(52) U.S. Cl.
    CPC .......... *A61B 5/04085* (2013.01); *A61B 5/046* (2013.01); *A61B 5/0464* (2013.01); *A61B 5/0472* (2013.01)

(56) References Cited

U.S. PATENT DOCUMENTS

| | | | |
|---|---|---|---|
| 5,782,238 A * | 7/1998 | Beitler | A61B 5/04085 600/372 |
| 6,416,471 B1 * | 7/2002 | Kumar | G06F 19/3418 600/300 |
| 7,130,681 B2 | 10/2006 | Gebhardt et al. | |
| 8,140,154 B2 | 3/2012 | Donnelly et al. | |
| 9,026,200 B2 | 5/2015 | Nagata et al. | |
| 9,750,433 B2 | 9/2017 | Hu et al. | |
| 2002/0026122 A1 * | 2/2002 | Lee | A61B 5/0006 600/523 |
| 2002/0087088 A1 | 7/2002 | Brodnick | |
| 2002/0138011 A1 * | 9/2002 | Rantala | A61B 5/04286 600/509 |
| 2002/0181680 A1 * | 12/2002 | Linder | A61B 5/0006 379/106.02 |
| 2005/0060001 A1 | 3/2005 | Singhal et al. | |
| 2007/0027388 A1 | 2/2007 | Chou | |
| 2007/0038057 A1 * | 2/2007 | Nam | A61B 5/04085 600/388 |
| 2007/0197925 A1 * | 8/2007 | Moore | A61B 5/0408 600/509 |
| 2008/0027338 A1 * | 1/2008 | Lu | A61B 5/0424 600/509 |
| 2009/0167286 A1 * | 7/2009 | Naylor | G01R 31/021 324/66 |
| 2010/0081950 A1 * | 4/2010 | Reinstadtler | A61B 5/0408 600/509 |
| 2010/0179452 A1 | 7/2010 | Srinivasan et al. | |
| 2011/0004088 A1 * | 1/2011 | Grossman | A61B 5/04085 600/382 |
| 2011/0066007 A1 | 3/2011 | Banet et al. | |
| 2011/0160601 A1 * | 6/2011 | Wang | A61B 5/04085 600/509 |
| 2011/0246144 A1 | 10/2011 | Tanaka | |
| 2015/0094558 A1 | 4/2015 | Russell | |
| 2016/0000379 A1 * | 1/2016 | Pougatchev | A61B 5/7275 600/479 |
| 2016/0066805 A1 * | 3/2016 | Scherf | A61B 5/7475 600/523 |
| 2016/0074667 A1 | 3/2016 | Sullivan et al. | |
| 2016/0120470 A1 | 5/2016 | Bogdanovich et al. | |
| 2016/0135706 A1 | 5/2016 | Sullivan et al. | |
| 2016/0331273 A1 * | 11/2016 | Armoundas | A61B 5/72 |
| 2017/0086693 A1 * | 3/2017 | Peterson | A61B 5/0006 |
| 2017/0087371 A1 | 3/2017 | Freeman et al. | |
| 2017/0095212 A1 | 4/2017 | Albadawi et al. | |
| 2017/0143977 A1 | 5/2017 | Kaib et al. | |
| 2017/0249445 A1 | 8/2017 | Devries et al. | |
| 2017/0281097 A1 | 10/2017 | Thakur et al. | |
| 2018/0014779 A1 | 1/2018 | Donnelly et al. | |
| 2018/0035919 A1 | 2/2018 | Koivisto et al. | |
| 2018/0064397 A1 | 3/2018 | Horikawa et al. | |
| 2018/0067565 A1 | 3/2018 | Yuen et al. | |

FOREIGN PATENT DOCUMENTS

| | | |
|---|---|---|
| CN | 103781404 A | 5/2014 |
| CN | 203662751 U | 6/2014 |
| CN | 204698545 U | 10/2015 |
| CN | 105832328 A | 8/2016 |
| JP | 2002159458 A | 6/2002 |

OTHER PUBLICATIONS

"Evaluation of a Threshold-based Tri-Axial Accelerometer Fall Detection Algorithm", Bourke et al, Gait & Posture, 2007.
"Optimal Placement of Accelerometers for the Detection of Everyday Activities", Ian et al, Sensors, 2013.
"Preprocessing Techniques for Context Recognition from Accelerometer Data", Figo et al, Personal and Ubiquitous Computing, 2010.

* cited by examiner

GARMENT AND CARDIAC DATA PROCESSING

CROSS-REFERENCE TO RELATED APPLICATION(S)

This application is a continuation-in-part of International Application No. PCT/CN2017/075572, filed on Mar. 3, 2017, which claims priority to Chinese Patent Application No. 201610150885.2, filed on Mar. 15, 2016, and is also a continuation-in-part of U.S. patent application Ser. No. 15/364,743, filed on Nov. 30, 2016, which has issued as U.S. Pat. No. 10,123,741, the contents of all of which are hereby incorporated by reference in their entireties.

TECHNICAL FIELD

This disclosure relates in general to smart wearable apparatuses, and in particular, wearable garments and electrocardiograph (ECG) signal processing.

BACKGROUND

In a cardiac cycle, a pacemaker, an atrium, and a ventricle are excited one after another with changes of bioelectricity. Various forms of graphs indicative of electric potential changes can be derived from the body surface using an electrocardiograph (ECG) device, which are called electrocardiograms.

For ECG monitoring, lead wires and electrodes can be attached or adhered to the body surface of an individual to obtain ECG signals. When more leads are used, more lead wires and electrodes are also needed. For example, at least three lead wires and three electrodes may be needed for limb leads, and 10 lead wires and 10 electrodes may be needed for 12 leads.

SUMMARY

Disclosed herein are methods and apparatuses for ECG signal collection at a wearable device for a user.

In an aspect, a method is disclosed for processing electrocardiograph (ECG) data using a garment. The method includes determining, by a processor, a current working lead from ECG leads formed in advance using flexible electrodes in the garment based on a current ECG monitor type, and receiving, by the processor through lead wires corresponding to the current working lead, ECG data collected by flexible electrodes corresponding to the current working lead.

In another aspect, a wearable apparatus is disclosed for processing electrocardiograph (ECG) data. The wearable apparatus includes at least two flexible electrodes, wherein the at least two flexible electrodes are capable of forming different leads based on predetermined configurations, at least two lead wires, and an ECG data collector configured to receive ECG data collected by the at least two flexible electrodes, wherein each of the at least two flexible electrodes connects to the ECG data collector via at least one of the at least two lead wires.

In another aspect, a non-transitory computer-readable medium is disclosed. The non-transitory computer-readable medium stores instructions which when executed by a computer system using a processor become operational with the processor for processing electrocardiograph (ECG) data using a garment. The non-transitory computer-readable medium includes instructions to determine, by the processor, a current working lead from ECG leads formed in advance using flexible electrodes in the garment based on a current ECG monitor type, wherein the current ECG monitor type is triggered by a user and received from a user interface, receive, by the processor through lead wires corresponding to the current working lead, ECG data collected by flexible electrodes corresponding to the current working lead, and based on the ECG data, determine a health status for a wearer of the garment.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Cardiac function is an essential component of health and certain cardiac conditions (e.g., cardiac arrhythmia, tachycardia, or bradycardia) can pose risks to an individual. Cardiac conditions can arise unexpectedly and when they do, time is of the essence. Fast detection and/or response to a cardiac condition can greatly improve outcomes for a person suffering from an adverse cardiac condition.

Systems for cardiac condition detection including wearable devices (e.g., a garment) disclosed herein address some of these technical challenges of automatically detecting cardiac conditions in a variety of circumstances. The garment can include flexible electrodes for detecting electrocardiogram measurements. For example, one or more machine learning models can be used to classify features extracted from the electrocardiogram measurements and determine a cardiac condition of a human wearing the garment. In some implementations, machine learning models can be trained based on measurements captured using a garment regularly worn by a human.

Quick action responsive to the detection of an adverse cardiac condition can be enabled. For example, alert signals (e.g., alert messages) indicating a cardiac condition of the human wearing the garment can be displayed and/or transmitted to alert the human, a health care provider, and/or a registered contact (e.g., friends and family) of the human to the occurrence of the cardiac condition.

Figure 1:
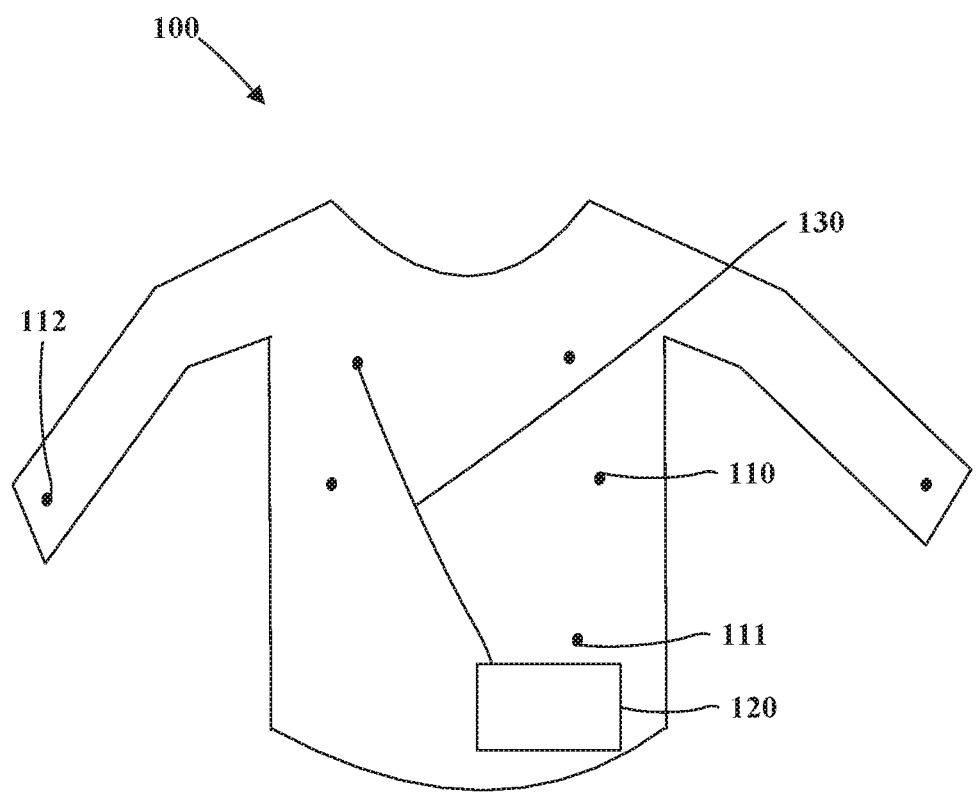
FIG. 1 is a diagram of an example garment according to implementations of this disclosure.

FIG. 1 is a diagram of an example garment 100 according to implementations of this disclosure. As shown in FIG. 1, the garment 100 can be provided with two or more flexible electrodes (shown as black dots in FIG. 1), an ECG data collector 120, and a lead wire 130 for connecting the flexible electrodes with the ECG data collector 120. The ECG data collector 120 can receive measurements from one or more sensors (e.g., the flexible electrodes). For example, the two or more flexible electrodes can include flexible electrodes 110, 111, and 112. In an implementation, for monitoring electrical activities of the heart of a wearer (e.g., using an electrical potential difference between two body surfaces of the wearer), the flexible electrodes can form ECG leads in advance. For example, each pair of the flexible electrodes can form a lead. For example, an anteroseptal lead can be formed by a flexible electrode on the garment 100 positioned at the fourth intercostal space at the right edge of the sternum and another flexible electrode on the garment 100 positioned at a central potential terminal (e.g., the Wilson Central Terminal) of the body. In some implementations, the lead wire 130 can be made of flexible conductive fibers.

It should be understood that the garment 100 shown in FIG. 1 can be implemented as other clothes for the upper body (e.g., a coat, a jacket, or a vest) or the lower body (e.g., pants, trousers, slacks, or shorts). The number and positions of the flexible electrodes provided for the garment 100 can also be determined or adjusted in accordance with the type of ECG monitoring (referred to as an "ECG monitor type") implemented by the garment 100.

In an implementation, the garment 100 can include a processor (not shown in FIG. 1). The processor can connect to the ECG data collector 120 for controlling the same. The processor herein can refer to any combination of any type of devices capable of manipulating or processing information. The processor can include a central processor (e.g., a central processing unit or CPU). The processor can also include a graphics processor (e.g., a graphics processing unit or GPU). The processor can also include a chip or integrated circuit for processing data. The processor can be distributed across multiple machines or devices (e.g., each machine or device having one or more processors) that can be coupled directly or across a wired or wireless network.

In another implementation, the garment 100 can further include a user interface (e.g., a control panel) that electrically connects to the ECG data collector 120 and the processor for receiving operation instructions from a user (e.g., the wearer, or an individual other than the wearer). The user interface herein can refer to an input/output device, such as a button, a switch, a key, a physical or virtual keyboard, a numerical keypad, a mouse, a trackball, a microphone, an LCD display, a touch-sensitive device (e.g., a touch screen), a sensor, or a gesture-sensitive input device. Any other type of interactive device can also be used herein for the user interface. For example, based on the operation instructions, the processor can determine an ECG monitor type. Based on the ECG monitor type, the processor can further determine a current working lead for collecting ECG data (e.g., ECG measurements). For another example, based on the operation instructions, the processor can determine a time interval for data collection (referred to as a "collection time interval") for flexible electrodes corresponding to the current working lead. Through lead wires corresponding to the current working lead, the processor can control the ECG data collector 120 to receive ECG data collected by the flexible electrode leads corresponding to the current working lead. The term "receive" used herein can refer to receiving, inputting, acquiring, retrieving, obtaining, reading, accessing, collecting, or any action in any manner for inputting information or data.

In addition, in some implementations, the garment 100 can further include a communication interface or device (not shown in FIG. 1) connected to the processor. The communication interface herein can refer to wired or wireless communication means, such as a serial port, a transponder/transceiver device, a modem, a router, a gateway, a circuit, a chip, a wired network adapter, a wireless network adapter, a Bluetooth adapter, an infrared adapter, a near-field communication (NFC) adapter, a cellular network chip, a body area network device, or any suitable type of device in any combination to provide functions of communication. For example, through the communication interface, the processor can send (e.g., via a wireless communication mean) the ECG data received by the ECG data collector 120 to a user terminal (e.g., a smartphone or a tablet computer) or a remote server computer (e.g., a server of a cloud service or a "cloud server"). Based on the ECG data received by the ECG data collector 120, the user terminal or the cloud server can generate an electrocardiogram and further determine a health status for the wearer of the garment 100. It should be noted that the wearer of the garment 100 and an owner of the user terminal can be the same individual or different individuals. For example, by using the garment as disclosed herein, a user (e.g., a child) can use a phone to monitor ECG for the wearer (e.g., a senior parent of the child) in real-time.

In an implementation, the garment 100 can further include a battery (not shown in FIG. 1). The battery can be used for powering the garment 100 and/or its peripherals. For example, the battery can be charged wirelessly or through a wired interface (e.g., a USB cable, or and AC adapter cable).

According to implementations of this disclosure, by using the flexible electrodes, lead wires, and ECG data collectors of the garment, ECG data can be collected for ECG monitoring. By using a processor in the garment, the ECG data collector of the garment can be controlled. Because the flexible electrodes can be positioned on the garment at corresponding locations in accordance with ECG lead placement for ECG monitoring in this disclosure, the ECG data for the ECG monitoring can be collected as long as the wearer is wearing the garment, and the health status of the wearer can be determined based on the collected ECG data. By performing the ECG monitoring through wearing the garment, interferences to the activities of the user can be minimized without adhering lead wires or electrodes on the body surfaces to obtain the ECG data, and the user can perform ECG monitoring in daily life. In addition, rhythm of the heart of the wearer can be detected when the wearer is wearing the garment (e.g., during a run), and an abnormal condition of the heart can be discovered in time, by which the user can be informed in time with the health status of the body, and the user experience can be improved.

Figure 2:
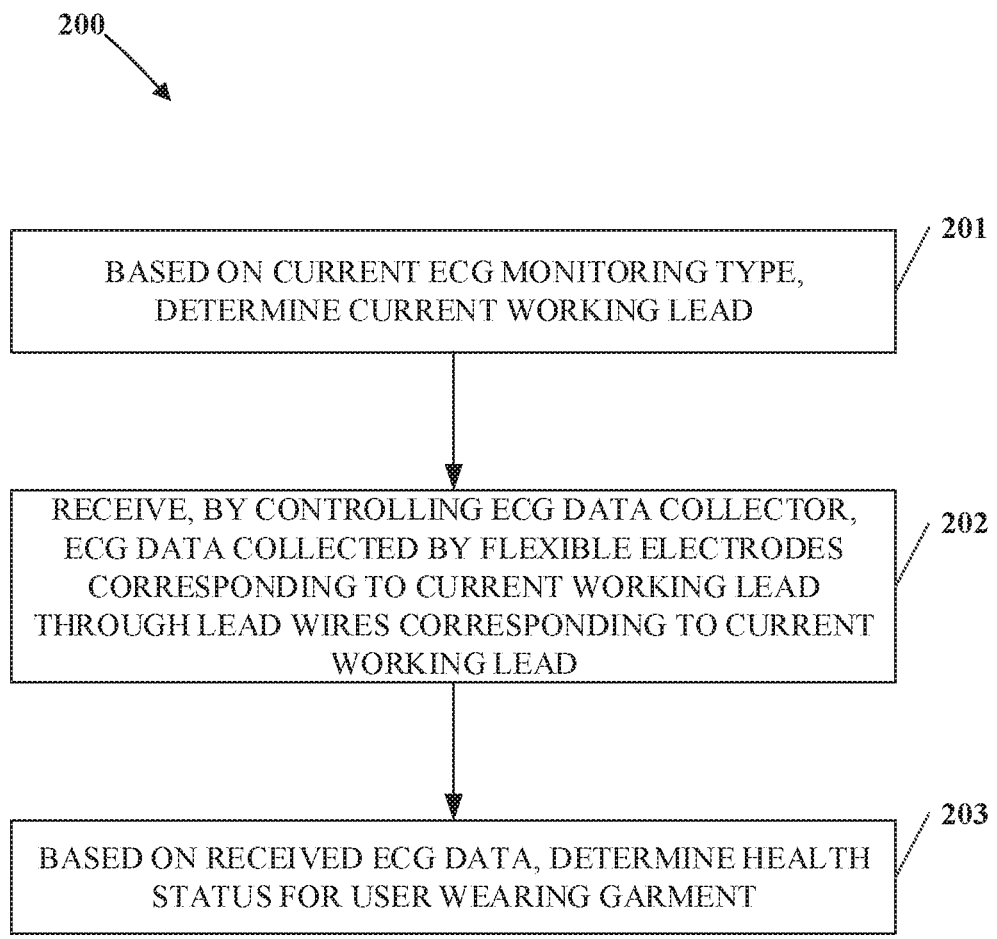
FIG. 2 is a flowchart of a first example process for processing ECG data according to implementations of this disclosure.

FIG. 2 is a flowchart of an example process 200 for processing ECG data according to implementations of this disclosure. The process 200 can be implemented for a garment (e.g., the garment 100 of FIG. 1). The garment 100 as described in the process 200 includes a processor. As shown in FIG. 2, the process 200 includes operations 201-203, which will be set forth as follows.

At operation 201, based on a current ECG monitor type, a current working lead is determined (e.g., by the processor).

At operation 202, ECG data collected by the current working lead is received. For example, the ECG data can be collected by flexible electrodes corresponding to the current working lead. For another example, the ECG data can be received by an ECG data collector controlled by the processor. For another example, the ECG data can be received via lead wires corresponding to the current working lead.

At operation 203, based on the received ECG data (e.g., received by the ECG data collector), a health status of a user wearing the garment is determined.

At the operation 201, in an implementation, the ECG monitor type can be determined based on operation instructions triggered by the user. In this implementation, the garment can include a user interface. The user interface can electrically connect to the ECG data collector and the processor. The processor can receive a first operation instruction triggered at the user interface by the wearer of the garment. For example, the first instruction can include a current ECG monitor type. Based on the first operation instruction, the processor can determine the ECG monitor type. Based on the current ECG monitor type, the processor can further determine the current working lead.

At the operation 201, in another implementation, the current ECG monitor type can be determined based on a message associated with a monitoring type (referred to as a "monitoring type message") sent from a user terminal. In this implementation, the garment can include a communication interface. The communication interface can electrically connect to the processor. A first instruction message sent from the user terminal can be received by the processor via the communication interface. For example, the first instruction message can include a current ECG monitor type. The processor can parse or analyze the first instruction message to obtain the current ECG monitor type. Based on the current ECG monitor type, the processor can further determine the current working lead.

For example, the ECG monitor type can be a type of ECG monitoring for obtaining the best respiratory wave (e.g., typically used in neonatal care). In this example, the current working lead can be determined or decided (e.g., by the processor) as a lead formed by the flexible electrode 111 and the flexible electrode 112. For each ECG monitor type, the corresponding working lead can be determined in accordance with medical bases by a garment provider, and pre-stored in the garment or the user terminal. When the current ECG monitor type is determined, the processor can determine the current working lead.

In the same example in which the ECG monitor type is the type of ECG monitoring for obtaining the best respiratory wave, at the operation 202, after determining the current working lead, the processor can control the ECG data collector 120 to obtain the ECG data collected by the flexible electrode 111 and the flexible electrode 112, through a lead wire between the ECG data collector 120 and the flexible electrode 112, and another lead wire between the ECG data collector 120 and the flexible electrode 111.

Figure 4:
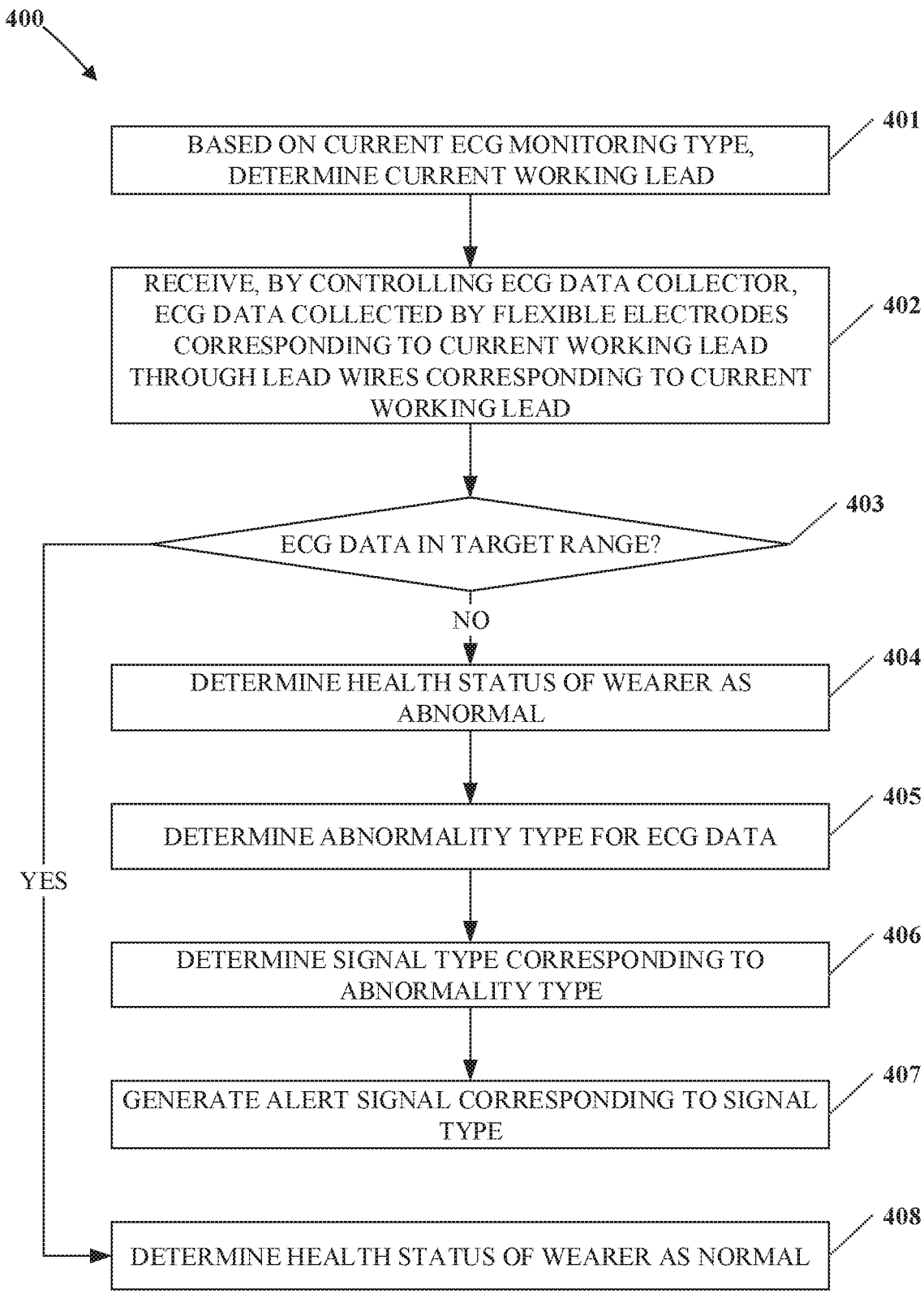
FIG. 4 is a flowchart of a third example process for processing ECG data according to implementations of this disclosure.

At the operation 203, the health status of the user can be determined based on the received ECG data in a process that will be shown and detailed in FIG. 4.

According to implementations of this disclosure, the ECG data for ECG monitoring of the current ECG monitor type can be collected using the flexible electrodes, lead wires, and ECG data collectors of the garment, without using lead wires or electrodes adhesive to body surfaces of an individual.

Figure 3A:
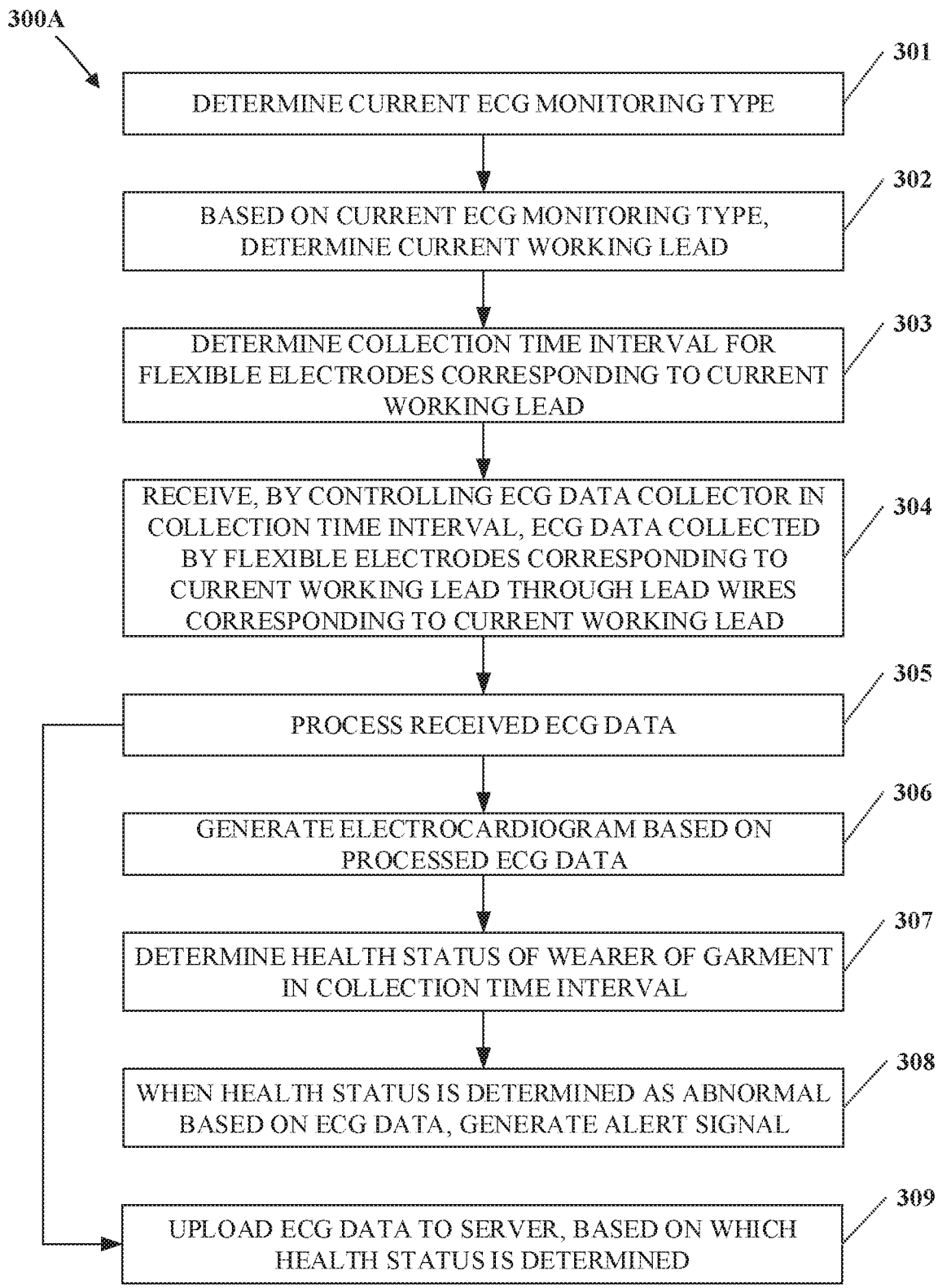
FIG. 3A is a flowchart of a second example process for processing ECG data according to implementations of this disclosure.
Figure 3B:
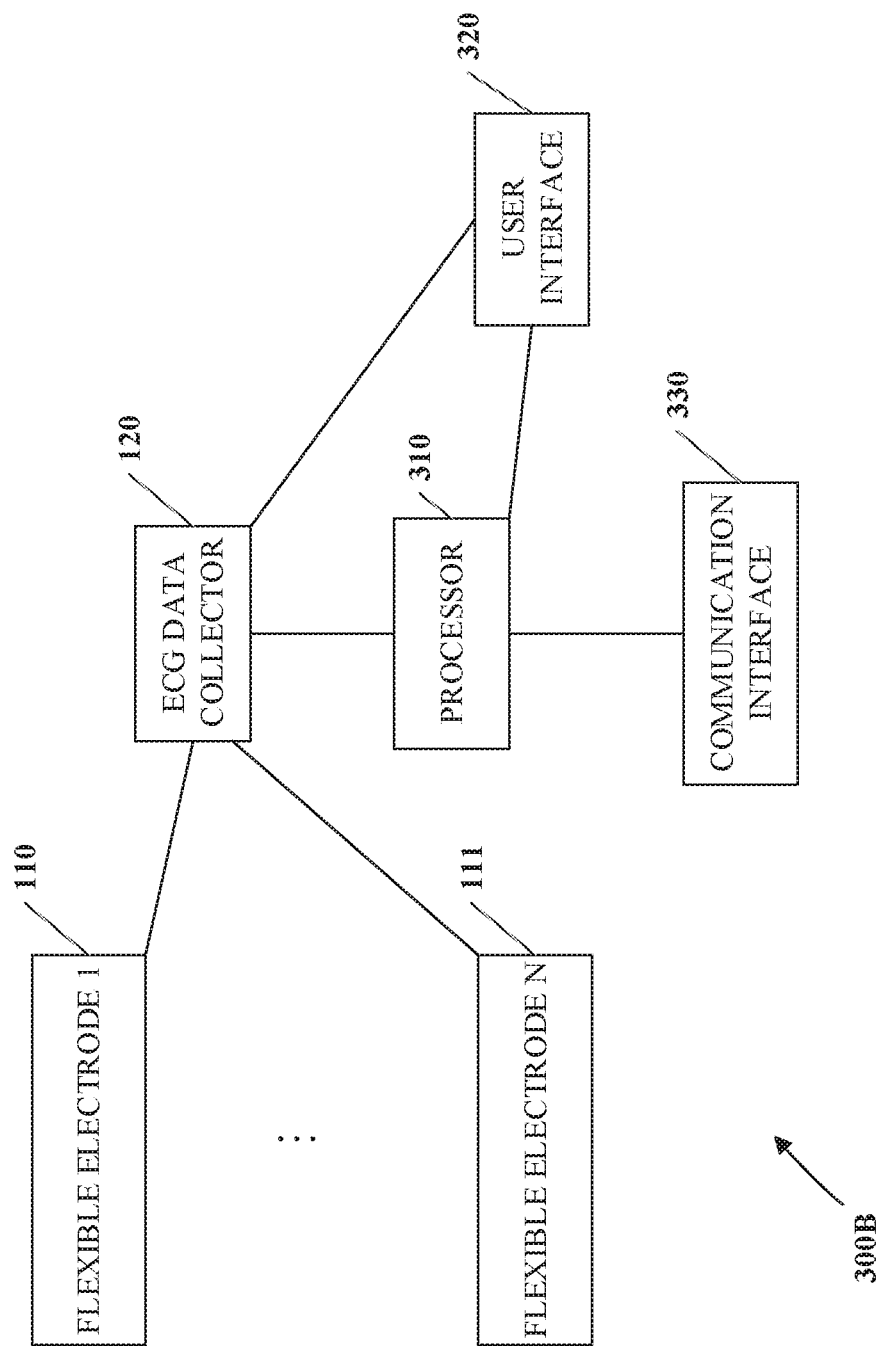
FIG. 3B is a diagram of components of an example garment according to implementations of this disclosure.

FIG. 3A is a flowchart of an example process 300A for processing ECG data according to implementations of this disclosure. FIG. 3B is a diagram of components of an example garment 300B according to implementations of this disclosure. The process 300A and the garment 300B will be described combining FIG. 1. For example, the garment 300B can include a processor 310, a user interface 320, a communication interface 330, an ECG data collector 120, and at least two flexible electrodes (e.g., flexible electrodes 110 and 111). The garment 300B can further include at least two lead wires. In some implementations, the garment 300B can further include a machine-readable storage medium (not shown in FIG. 3B).

The flexible electrodes (e.g., the flexible electrodes 110 and 111) can connect to the ECG data collector 120 via lead wires. For example, two flexible electrodes (e.g., the flexible electrodes 110 and 111) of the at least two flexible electrodes can form an ECG lead (e.g., a precordial lead, lead I, lead II, lead III, lead aVR, lead aVL, or lead aVF).

The machine-readable storage medium can include a memory. The memory herein can refer to any device capable of storing codes (or instructions) and data that can be accessed by the processor. For example, the memory herein can be a random access memory (RAM), a read-only memory (ROM), an optical/magnetic disc, a hard drive, a solid state drive, a flash drive, a security digital (SD) card, a memory stick, a compact flash (CF) card, or any combination of any suitable type of storage device. The memory herein can also be distributed across multiple machines or devices, such as a network-based memory or cloud-based memory.

The machine-readable storage medium can include a non-transitory or non-volatile machine-readable storage medium. The non-transitory machine-readable storage medium can be in the form of any suitable non-transitory computer-readable medium, such as a hard disc drive, a memory device, a solid state drive, a flash drive or an optical drive. When present, the non-transitory machine-readable storage medium can provide additional memory when high processing requirements exist. For example, the non-transitory machine-readable storage medium can store instructions to process ECG data. In some implementations, the non-transitory machine-readable storage medium can be a shared device that can be accessed by other components, devices, or systems.

The processor 310 and the machine-readable storage medium can be connected via an internal bus (not shown in FIG. 3B). The communication interface 330 can communicate data or instructions with other components, devices, or systems.

As shown in FIG. 3A, the process 300A includes operations 301-309, which will be set forth as follows.

At operation 301, the current ECG monitor type is determined (e.g., by the processor 310).

At operation 302, based on the current ECG monitor type, the current working lead is determined (e.g., by the processor 310).

At operation 303, a collection time interval for flexible electrodes corresponding to the current working lead is determined (e.g., by the processor 310).

At operation 304, ECG data collected by the flexible electrodes corresponding to the current working lead is received in the collection time interval. For example, the ECG data can be received via lead wires corresponding to the current working lead. For another example, the ECG data can be received by the ECG data collector 120 controlled by the processor 310.

At operation 305, processed ECG data is determined by processing (e.g., by the processor 310) the received (e.g., by the ECG data collector 120) ECG data. In some implementations, operations 306-308 can be performed after the operation 305. In some implementations, operation 309 can be performed after the operation 305, as an alternative of or in addition to the operations 306-308.

At operation 306, an electrocardiogram is generated (e.g., by the processor 310) based on the processed ECG data.

At operation 307, a health status of the wearer of the garment in the collection time interval is determined (e.g., by the processor 310) based on the electrocardiogram.

At operation 308, if the health status of the wearer of the garment is determined as abnormal based on the ECG data or the electrocardiogram, an alert signal is generated.

At operation 309, the ECG data is uploaded to a server (e.g., a cloud server), based on which the health status of the wearer of the garment is determined. For example, the ECG data can be uploaded by the processor 310 using the communication interface 330 (e.g., via a wireless communication mean). The wireless communication means herein can include any combination of, for example, a WiFi connection, a Bluetooth connection, a ZigBee connection, an NFC connection, and a radio-frequency (RF) connection. For another example, the health status of the wearer of the garment can be determined by a user capable of accessing the cloud server.

At the operation 301, in an implementation, a current ECG monitor type can be determined based on an operation triggered by the user directing to the garment. As shown in FIG. 3B, the wearer of the garment can trigger an operation for selecting the current ECG monitor type via the user interface 320. For example, the wearer of the garment can push a button (e.g., on the user interface 320) provided with the garment for ECG monitor type to trigger the operation. When the wearer of the garment selects the current ECG monitor type via the user interface 320, the processor 310 can determine the current ECG monitor type.

In another implementation, the current ECG monitor type can be determined based on a monitoring type message sent by a user terminal. When the garment receives the monitoring type message sent from the user terminal via the communication interface 330, the processor 310 can determine the current ECG monitor type by parsing or analyzing the message. By determining the current ECG monitor type using the user terminal, the operation can become more user-friendly, and power consumption and cost of the garment can be reduced to a certain degree.

At the operation 303, in an implementation, to make the ECG data collected by the flexible electrodes more pertinent and avoid collecting excessive non-usable ECG data that might interfere with the usable ECG data for the wearer of the garment, the collection time interval can be determined for the flexible electrodes prior to starting the ECG monitoring. In some implementations, the flexible electrodes can collect the ECG data periodically. In some other implementations, the flexible electrodes can be configured to collect the ECG data during a fixed time interval of a day. For example, the flexible electrodes can be configured to collect the ECG data for half an hour once in every two hours. For another example, the flexible electrodes can be configured to collect the ECG data during a time interval of arising from bed in every morning. For another example, the flexible electrodes can be configured to collect the ECG data continuously in 24 hours to perform dynamic ECG monitoring for the wearer of the garment.

In an implementation, as shown in FIG. 3B, the collection time interval for the flexible electrode to collect the ECG data can be determined using the user interface 320 and the processor 310 on the garment. For example, the processor 310 can receive a second operation instruction triggered at the user interface 320 by the wearer of the garment. The second operation instruction can include the collection time interval for the flexible electrodes corresponding to the current working lead. Based on the second operation instruction, the processor 310 can determine the collection time interval for the flexible electrodes corresponding to the current working lead. For another example, the collection time interval for the flexible electrodes to collect the ECG data can also be determined using voice control.

In another implementation, based on a message associated with a monitoring time (referred to as a "monitoring time message") sent from the user terminal, the processor 310 can determine the collection time interval for the flexible electrodes to collect the ECG data. When the garment receives the monitoring time message sent from the user terminal via the communication interface 330, the processor 310 can determine a time for the flexible electrodes to collect the ECG data based on the message.

Details of the operation 304 can be referred to FIG. 2 and related description, which will not be further described hereinafter.

At the operation 305, as shown in FIG. 3B, the processor 310 can process the ECG data received by the ECG data collector 120. For example, the received ECG data can be filtered. For another example, the received ECG data can be segmented for obtaining a median value in each segment. By processing the ECG data, the data size can be reduced, and the computation cost can be lowered for the later data processing of the garment.

Methods and processes at the operations 306 and 307 for generating the electrocardiogram using the collected ECG data and determining the health status based on the electrocardiogram will not be further detailed in this disclosure.

At the operation 308, in an implementation, if the health status of the wearer of the garment is determined as abnormal based on the ECG data, the processor 310 can generate an alert signal. In some implementations, the alert signal can include an acoustic alert signal and/or a visual (or optical) alert signal. For example, a beep sound can be generated to indicate the wearer of the garment that the current ECG data is abnormal. For another example, a signal indicator on the user interface 320 can be lighted to indicate the wearer of the garment that the current ECG data is abnormal.

At the operation 309, in an implementation, as shown in FIG. 3B, by uploading the processed ECG data via the communication interface 330 to the cloud server, additional services can be provided to the wearer of the garment. For example, a user accessing the cloud server (e.g., a medical expert) can determine the health status of the wearer of the garment based on the processed ECG data, and propose a therapy program.

According to some implementations of this disclosure, the ECG data can be collected by the flexible electrodes in the collection time interval, by which the collected ECG data can become more pertinent, and non-usable data can be minimally collected to avoid interference with the usable ECG data for the user. In addition, when the health status of the user is determined as abnormal based on the electrocardiogram, an alert signal can be generated as an early warning for abnormal body conditions. Further, by uploading the ECG data to cloud servers, more additional services can be provided to the wearer of the garment.

Figure 3C:
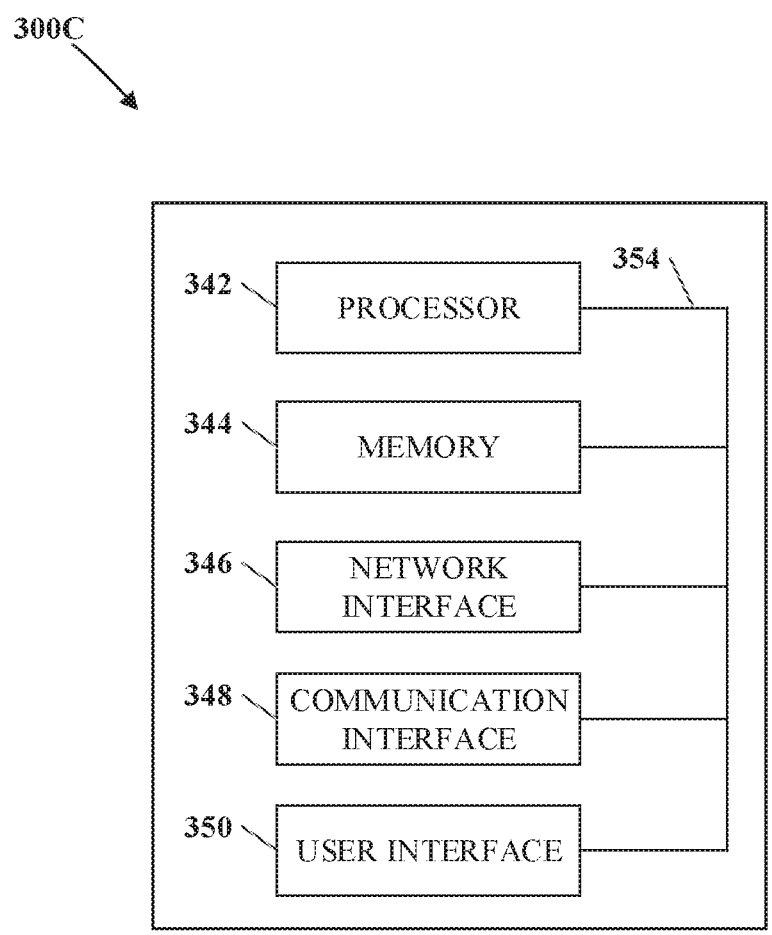
FIG. 3C is a block diagram of an example user terminal according to implementations of this disclosure.

FIG. 3C is a block diagram of an example user terminal 300C according to implementations of this disclosure. For example, the user terminal 300C can include any combination of a personal computer, a laptop computer, a tablet computer, a phone, a personal data assistant (PDA), or a wearable computing device (e.g., a watch, or glasses). The user terminal 300C can be used to control the garment for ECG monitoring (e.g., the garment 300B), and receive data from the garment to generate an electrocardiogram and further determine a health status for the wearer of the garment.

As shown in FIG. 3C, the user terminal 300C includes a processor 342, a memory 344, a network interface 346, a communication interface 348, and a user interface 350. In some implementations, the user terminal 300C can further include a battery (not shown in FIG. 3C). For example, the battery can be charged wirelessly or through a wired interface (e.g., a USB cable, or and AC adapter cable).

The processor 342 can be similar to the processor 310 in FIG. 3B, and the memory 344 can be similar to the memory (not shown in FIG. 3B) included in the garment 300B. The processor 342 can access and manipulate data stored in the memory 344 via a bus 354. The codes and data stored in the memory 344 can include an operating system (OS) and one or more application programs (e.g., apps) for processing and/or outputting the data.

The network interface 346 can be used to transmit and receive data to and from the garment via a wired and/or wireless computing network (e.g., a cellular data network, a WiFi wireless LAN, an Ethernet LAN, and/or a WAN, such as the Internet). In some implementations, the network interface 346 can implement a network protocol (e.g., IPv4 or IPv6) for communications with other computing devices via a network. In some implementations, the network interface 346 can forward ("upload") the data received from the garment to a cloud server, or receive ("download") feedback data from the cloud server.

The communication interface 348 can enable wired or wireless communications with the garment. For example, the communication interface 348 can be used to receive ECG data from the garment (e.g., via transmissions from the communication interface 330 of the garment 300B). In some implementations, the communication interface 348 can be used to receive information (e.g., alert signals) for indicating a user from the garment. For example, the communication interface 348 can include any combination of a Bluetooth interface, a ZigBee interface, a WiFi interface, an NFC interface, and an RF interface. In some implementations, the communication interface 348 and the network interface 346 can be implemented as a single device.

The user interface 350 can include a display (e.g., a touchscreen display, an LCD display, or a CRT monitor) for presenting alerts or other messages to the wearer of the garment or another user assisting the wearer, and detecting control inputs (e.g., operations or gestures performed by the user). For example, the user interface 350 can include buttons or switches enabling a person to manually turn the user terminal 300C on and off, or adjust sound volume. For another example, the user interface 350 can include a keyboard, a mouse, a trackpad, and/or a microphone for receiving user input.

Figure 3D:
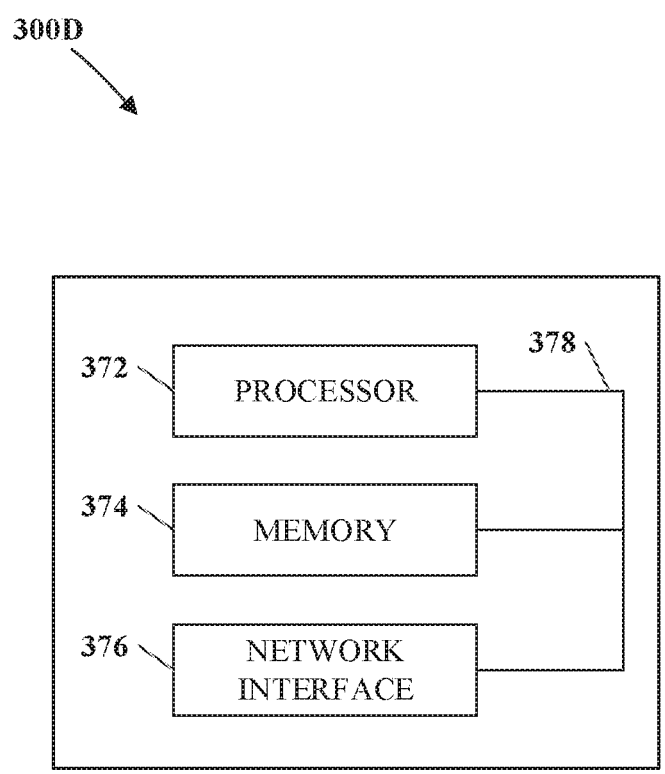
FIG. 3D is a block diagram of an example server according to implementations of this disclosure.

FIG. 3D is a block diagram of an example server 300D according to implementations of this disclosure. For example, the server 300D can include any combination of a microcomputer, a mainframe computer, a supercomputer, a general-purpose computer, a special-purpose/dedicated computer, an integrated/embedded computer, a database computer, a remote server computer, or a computing service provider (e.g., a website, or a cloud service) provided by a computing service. The server 300D can be used to receive data from the garment, generate an electrocardiogram, and further determine a health status for the wearer of the garment or send the electrocardiogram to another user (e.g., a medical expert) for determining the health status.

As shown in FIG. 3D, the server 300D includes a processor 372, a memory 374, and a network interface 376, which are similar to the processor 342, the memory 344, and the network interface 346 in FIG. 3C, respectively. The processor 372 can access and manipulate data in stored in the memory 374 via a bus 378, or via computing network communications (e.g., where the memory includes a database server in separated from the processor 372 by a computing network).

The network interface 376 can be used to receive data transmitted from the garment (e.g., via the communication interface 330) or the user terminal (e.g., via the network interface 346). For example, ECG data collected by the garment or the electrocardiogram generated by the user terminal (or the garment) can be received by the server 300D via the network interface 376. Other data (e.g., the received ECG data, the electrocardiogram, the health status, or the alert signal) can be transmitted by the server 300D to a registered device (e.g., the garment, the user terminal, or a third user terminal).

FIG. 4 is a flowchart of an example process 400 for processing ECG data according to implementations of this disclosure. The process 400 can be implemented for a garment (e.g., the garment 100 of FIG. 1). The garment 100 as described in the process 400 includes a processor. As shown in FIG. 4, the process 400 includes operations 401-408, which will be set forth as follows.

At operation 401, based on a current ECG monitor type, a current working lead is determined (e.g., by the processor).

At operation 402, ECG data collected by flexible electrodes corresponding to the current working lead is received by an ECG data collector. For example, the ECG data can be received through lead wires corresponding to the current working lead. For another example, the ECG data collector can be controlled by the processor.

At operation 403, it is determined (e.g., by the processor) whether the ECG data received by the ECG data collector is within a target range of ECG data associated with the wearer of the garment. The target range of ECG data can be indicative of normal heart activities (e.g., electrical heart activities) of the wearer of the garment. If it is determined that the ECG data received by the ECG data collector is within the target range of ECG data associated with the wearer of the garment, operation 408 is performed; otherwise, operation 404 is performed.

At the operation 404, it is determined (e.g., by the processor) that a health status of the wearer of the garment is abnormal.

At operation 405, an abnormality type of the ECG data is determined (e.g., by the processor).

At operation 406, a signal type corresponding to the abnormality type is determined (e.g., by the processor).

At operation 407, an alert signal corresponding to the signal type is generated (e.g., by the processor).

At the operation 408, if the ECG data received by the ECG data collector is within the target range of ECG data associated with the wearer of the garment, the health status of the wearer of the garment is determined (e.g., by the processor) as normal.

Details of the operations 401 and 402 can be referred to FIG. 2 and related description, which will not be further described hereinafter.

At the operation 403, in an implementation, the garment can include a storage unit or device. The target ranges of heart activities (e.g., heart rates or cardiac rhythms) for individuals of different ages and sexes can be different, in accordance with which the garment can be provided with predetermined multiple target ranges of ECG data for wearers of the garment. For example, the target range of ECG data for the wearer of the garment can be determined by testing during a test time interval and stored in the storage device. In later ECG monitoring, based on the target range of ECG data of the wearer of the garment, the processor can determine the health status of the wearer.

At the operation 405, for example, the abnormality type of the ECG data can include at least one of cardiac arrhythmia, tachycardia, bradycardia, sinus tachycardia, and sinus bradycardia. In some implementations, the abnormality type can be determined based on the ECG data using a machine learning model. The machine learning model can be predetermined based on training data. For example, features can be determined based on the ECG data, and the features can be processed with the machine learning model to classify an ECG abnormality type. For example, a feature can be determined based on an estimate of an entropy of a normalized power spectral density of a sequence of the ECG data. For another example, a feature can be determined based on an estimate of a power spectral density within a frequency band for a sequence of the ECG data. The training and using of the machine learning model will be detailed in the later description.

At the operation 406, in an implementation, the alert signal type corresponding to each abnormality type can be predetermined. For example, if the abnormality type is sinus tachycardia, the alert signal type can be determined as a vibration signal in accordance with the predetermined configuration. For another example, if the abnormality type is tachycardia, the alert signal type can be determined as an optical signal of lighting an indicator in accordance with the predetermined configuration. For another example, if the abnormality type is a cardiac arrhythmia, the alert signal type can be determined as an acoustic signal in accordance with the predetermined configuration. In some implementations, the alert signal type can be determined based on a risk level of each abnormality type to a human body. For example, if an abnormality type has a higher risk level to the human body, the alert signal corresponding to the abnormality type can be determined as vibration plus voice reminder to cause the user to pay sufficient attention.

At the operation 407, when the alert signal type is determined, the processor can generate the alert signal. For example, if the alert signal type is determined as vibration, the processor can control a motor provided with the garment to vibrate (e.g., with regularity).

In some implementations, the process 400 can be applied to monitor cardiac condition continuously over a long period of time while the garment is being worn. For example, continuous monitoring can increase the chances of detecting unexpected emergency cardiac conditions, such as ventricular fibrillation. In some implementations, the process 400 can be applied to monitor cardiac condition episodically within a short time frame in response to a triggering event (e.g., a measurement command issued through a user interface of the garment or the user terminal), which can conserve power consumption and/or computation cost.

According to implementations of this disclosure, the target range of ECG data for the wearer of the garment can be determined by the garment for different wearers. Based on the target range of ECG data for the wearer of the garment, the health status of the wearer can be determined. When the health status of the wearer is abnormal, an alert signal corresponding to the abnormality type can be generated for the wearer to determine an abnormal condition of the body based on the alert signal, by which user experience can be improved.

Figure 5:
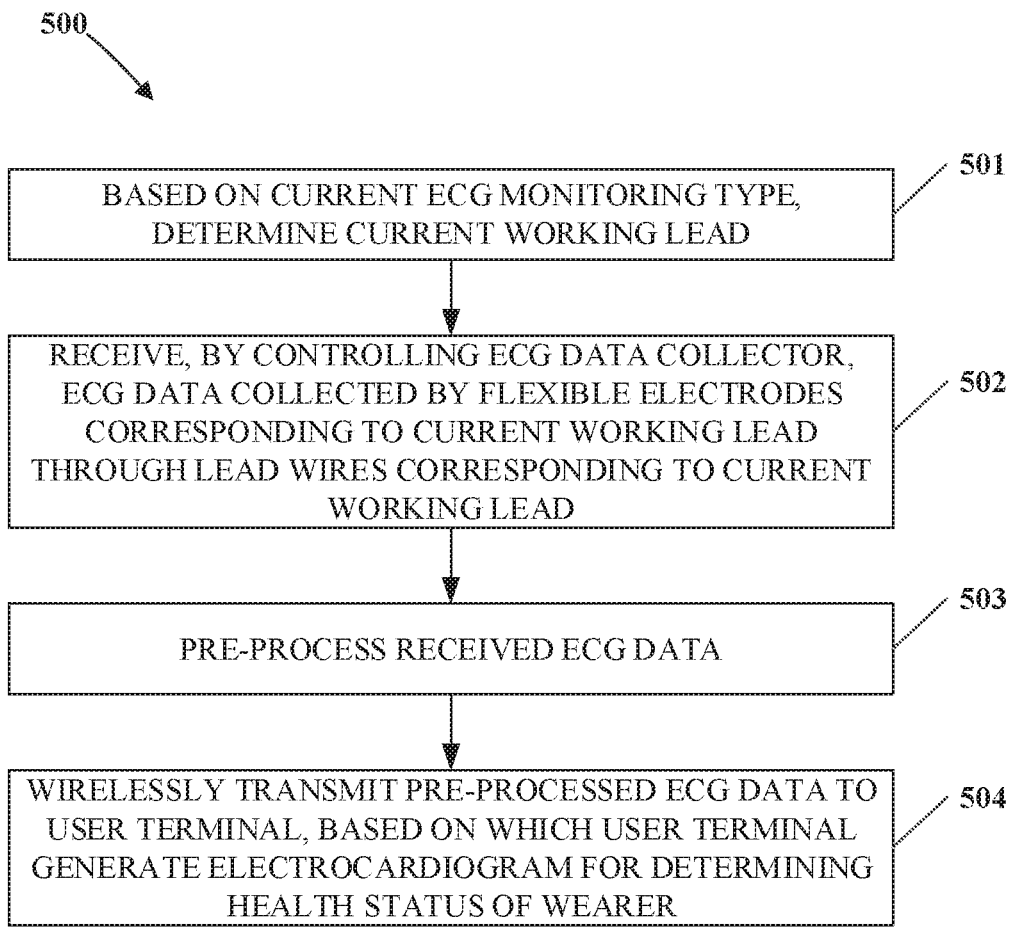
FIG. 5 is a flowchart of a fourth example process for processing ECG data according to implementations of this disclosure.

FIG. 5 is a flowchart of an example process 500 for processing ECG data according to implementations of this disclosure. The process 500 can be implemented for a garment (e.g., the garment 300B of FIG. 3B). As shown in FIG. 5, the process 500 includes operations 501-504, which will be set forth as follows.

At operation 501, based on a current ECG monitor type, a current working lead is determined (e.g., by a processor).

At operation 502, ECG data collected by flexible electrodes corresponding to the current working lead is received by an ECG data collector. For example, the ECG data can be received through lead wires corresponding to the current working lead. For another example, the ECG data collector can be controlled by the processor.

At operation 503, the ECG data received by the ECG data collector is pre-processed (e.g., by the processor).

At operation 504, the pre-processed ECG data is transmitted to a user terminal. For example, the pre-processed ECG data can be transmitted by the processor (e.g., via a wireless communication mean). The user terminal can generate an electrocardiogram based on the pre-processed ECG data. The electrocardiogram can be used for determining a health status of the wearer of the garment.

Details of the operations 501 and 502 can be referred to FIGS. 2-3A and related description, which will not be further described hereinafter.

At the operation 503, as shown in FIG. 3B, the processor 310 of the garment can pre-process the ECG data received by the ECG data collector 120. In some implementations, the pre-processing can including discarding non-usable ECG data for reducing the data size. For example, to reduce the ECG data size, the processor 310 can segment the ECG data received by the ECG data collector 120, and determine a median value for each segment. By performing the pre-processing, when transmitting (e.g., via a wireless connection) the pre-processed ECG data to the user terminal, the power consumption of the garment can be reduced.

At the operation 504, the processor 310 can wirelessly transmit the pre-processed ECG data to the user terminal via the communication interface 330. For example, the communication interface 330 can use a low-energy Bluetooth connection (e.g., a Bluetooth Low Energy or "BLE" connection). For another example, the communication interface 330 can use other short-range or long-range communication means to transmit the pre-processed ECG data to the user terminal. Based on the pre-processed ECG data, the user terminal can generate the electrocardiogram and determine the health status for the wearer of the garment. In some implementations, the user terminal can also upload the pre-processed ECG data to a cloud server for providing additional services to the wearer.

According to implementations of this disclosure, the processor can pre-process the ECG data and transmit the pre-processed ECG data to the user terminal, by which the power consumption of the garment can be reduced, and computation complexity of the garment can be lowered.

As previously described in FIGS. 4-5, to determine a health status (e.g., a cardiac condition or an abnormality type of ECG) for a wearer of the garment, machine learning models can be trained and used. The training of the machine learning models can be performed off-line to ECG training data (e.g., predetermined ECG measurement data for training). The ECG training data can include associated labels. The ECG training data can be acquired over a period of time from one or more individuals (e.g., the wearer or other individuals). The ECG training data can be used to configure and/or calibrate methods (e.g., the processes 200-500) and apparatuses (e.g., the garments 100 and 300A) for determining the health status of the wearer.

In some implementations, the training process for a machine learning model can include three stages: a pre-processing stage, a feature extraction stage, and a classifier training stage. At the pre-processing stage, the ECG training data are pre-processed. At the feature extraction stage, features are extracted from the pre-processed ECG training data. At the classifier training stage, an ECG classifier is trained based on the extracted features. For example, the training process can be implemented by a garment (e.g., the garment 100 or 300A), a user terminal (e.g., the user terminal 300C), or a server (the server 300D).

For example, at the pre-processing stage, ECG data collected from one or more individuals (e.g., the wearer or other individuals) can be pre-processed using various pre-processing techniques. The pre-processing techniques can include suppression of noise in the ECG measurement data (e.g., due to power line interference or possible motion artifacts). The pre-processing techniques can also include filtering a sequence of ECG measurements (e.g., using a moving average over a sliding time window, using an exponential moving average, using Wiener Filtering, and/or using other forms of adaptive filtering).

For example, at the feature extraction stage, the features can be extracted based on the pre-processed ECG data. For example, a feature can be extracted based on an estimate of an entropy of a normalized power spectral density of a sequence of the ECG measurements. For another example, a feature can be extracted based on an estimate of a power spectral density within a frequency band for a sequence of the ECG measurements. In some implementations, the extracted features can include, for example, PQRST complex fiducial points, R peak to R peak related features (e.g., a heart rate), fast Fourier transform (FFT) based features, wavelet transform based features, or autocorrelation discrete cosine transform (AC-DCT) based features. The features can be extracted from a sequence of ECG measurements collected from a lead (e.g., a precordial lead, lead I, lead II, lead III, lead aVR, lead aVL, or lead aVF) over a window of time.

For example, at the classifier training stage, the ECG classifier can be trained based on the extracted features and/or the pre-processed ECG data. For example, the ECG training data can be associated with labels of a cardiac condition experienced by an individual at the time the ECG data being collected. The ECG classifier can be implemented any combination of any type of machine learning models, such as, for example, a support vector machine (SVM), a Bayesian model, or a decision tree. For example, for a supervised learning model, the ECG classifier can be trained using the labels associated with cardiac conditions.

In some implementations, the ECG training data can include ECG measurements that have been gathered from the wearer of the garment. For example, personalized adaptation to aspects of an individual's activity patterns and/or cardiac response can be accomplished by analyzing the ECG training data from the same individual that will be monitored using the garment. For another example, a user can be prompted through a user interface of a user terminal (e.g., the user interface 350 of the user terminal 300C) to select training labels for a cardiac condition of the user, when the ECG training data is being collected with the garment.

In some implementations, the ECG training data can include ECG measurements that have been gathered from multiple individuals using similar garments or different measurement devices (e.g., another ECG monitor device). The similar garments or the different measurement devices can be operated in controlled environments to generate ECG training data and associate the same with assigned labels indicative of cardiac conditions.

In some implementations, the classifying process for determining a health status (e.g., a cardiac condition) using a machine learning model can include three stages: a pre-processing stage, a feature extraction stage, and a determining stage. The pre-processing stage and the feature extraction stage of the classifying process can be similar to the corresponding stages in the training process of the machine learning model. At the determination stage, one or more machine learning models trained using the ECG training data can be utilized to determine a cardiac condition for the wearer of the garment. For example, the classifying process can be implemented by a garment (e.g., the garment 100 or 300A), a user terminal (e.g., the user terminal 300C), or a server (the server 300D).

At the determination stage, the cardiac condition of the wearer can be determined using the ECG data and a machine learning model previously determined based on ECG training data. For example, a cardiac condition can be determined by inputting features extracted at the feature extraction stage to the trained machine learning model (e.g., the ECG classifier). In some implementations, the cardiac condition can be determined using the machine learning model based on an estimate of a power spectral density within a frequency band for a sequence of the ECG measurements. In some implementations, the cardiac condition can be determined using the machine learning model based on an estimate of an entropy of a normalized power spectral density of a sequence of the ECG measurements. In some implementations, the cardiac condition can be determined using the machine learning model based on an estimate of a fiducial point of a QRS complex in a sequence of the ECG measurements.

Figure 6:
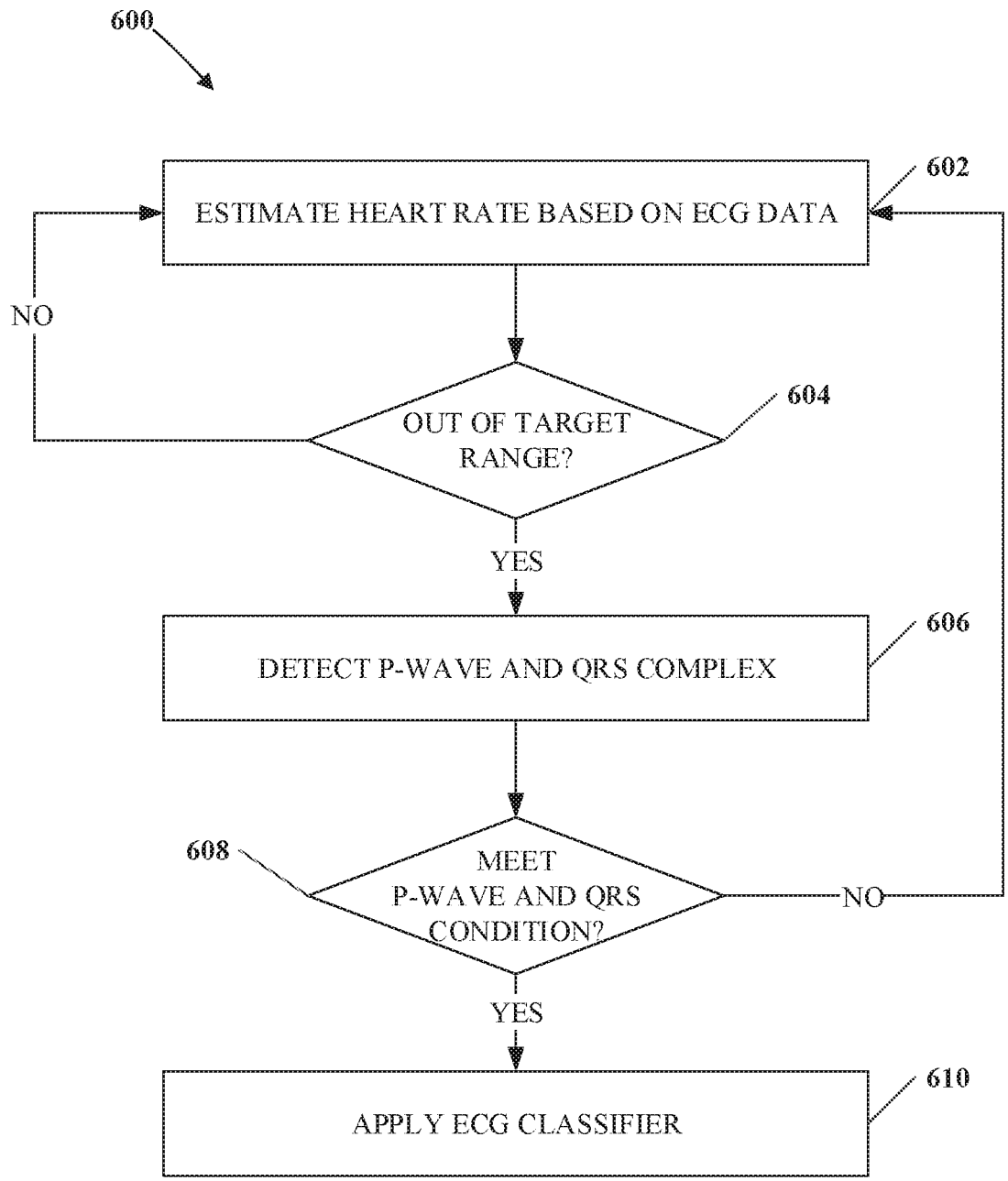
FIG. 6 is a flowchart of an example process for detecting a cardiac condition according to implementations of this disclosure.

FIG. 6 is a flowchart of an example process 600 for detecting a cardiac condition. The cardiac condition can include ventricular fibrillation and/or a supraventricular tachycardia condition. For example, the process 600 can detect a ventricular fibrillation condition based on estimating a heart rate (e.g., in beats-per-minute, or "BPM") that is outside of a target range for the heart rate. The heart rate can be outside of the target range by, for example, far above a maximum heart rate, or unreadable due to an unrecognizable morphology of an ECG signal (e.g., R peaks cannot be reliably identified). For example, the process 600 can be implemented by a garment (e.g., the garment 100 or 300A), a user terminal (e.g., the user terminal 300C), or a server (the server 300D). The process 600 includes operations 602-610 described as follows.

At operation 602, the heart rate of the wearer can be estimated based on ECG data collected by the garment. For example, a number of R peaks detected within a time window of known duration for one or more leads (e.g., a precordial lead or lead I) from a sequence of ECG measurements can be counted to estimate the heart rate of the wearer. In some implementations, the heart rate can be estimated based on determining an autocorrelation function for a sequence of the ECG measurements at various lags. In some implementations, the ECG data can be pre-processed (e.g., in a way similar to the pre-processing stage of the above-described classifying process). In some implementations, features can be extracted from the ECG data (e.g., in a way similar to the feature extraction stage of the above-described classifying process).

At operation 604, the estimated heart rate can then be compared to a target range for the wearer to determine whether the estimated heart rate is out of the target range. For example, the target range can be between 60 and 100 BPM for a ventricular fibrillation condition associated with the wearer. When the estimated heart rate is substantially above the target range, it can be indicative of a possible abnormality type of the ECG data. For example, if the estimated heart rate is in a range between 150 and 500 BPM, it can be indicative of the wearer is having a ventricular fibrillation condition. For another example, if the estimated heart rate is in a range between 110 and 264 BPM, it can be indicative of the wearer is having a supraventricular tachycardia condition.

If it is determined that the estimated heart rate is out of the target range, the process 600 proceeds to the operation 606. Otherwise, the process 600 goes back to the operation 602. The target range of heart rates can vary with the cardiac conditions (e.g., abnormality types), and can be adjusted accordingly. In implementations where ECG training data for the wearer of the garment has been collected, the applicable target ranges for the various cardiac conditions can be narrowed and tailored to the wearer.

At operation 606, a P-wave and QRS complex within a time window for one or more leads (e.g., a precordial lead and/or lead I) are detected from a sequence of ECG measurements. For example, the Pan-Tompkins algorithm can be used to identify a QRS complex and P-Wave. For another example, a wavelet transform (e.g., using a symlet 4 wavelet) can be additionally used for identifying the QRS complex.

At operation 608, it is determined whether a P-wave and QRS complex condition is met. The P-wave and QRS complex condition can use the P-wave and/or QRS complex detected at the operation 606 to determine a cardiac condition (e.g., an abnormality type) for the wearer. In some implementations, for detection of different cardiac conditions, the P-wave and QRS complex condition can include different criteria. The different criteria can be compared against the detected P-wave and QRS complex in sequence or in parallel. When the P-wave and QRS complex condition is met (e.g., all criteria for detecting different cardiac conditions have been compared against the detected P-wave and QRS complex), the process 600 proceeds to the operation 610; otherwise, the process 600 goes back to the operation 602.

For example, when the P-wave and the QRS complex have been successfully identified at the operation 606, it can be determined that an occurrence of ventricular fibrillation is not likely, in which the P-wave and QRS complex condition for determining a ventricular fibrillation condition is not met, and the process 600 can continues to use other criteria for detecting other cardiac conditions, or can go back to the operation 602.

For another example, when no P-wave has been identified at the operation 606, it can be determined that an occurrence of supraventricular tachycardia is not likely, in which the P-wave and QRS complex condition for determining a supraventricular tachycardia condition is not met, and the process 600 can continues to use other criteria for detecting other cardiac conditions, or can go back to the operation 602. For another example, a lack of a detectable P-wave can be associated with a potential atrioventricular nodal reentrant tachycardia (AVNRT) condition or an atrial fibrillation condition, and criteria for determining a potential AVNRT condition and/or a potential atrial fibrillation condition can be further compared to the P-wave and the QRS complex, details of which will not be further described hereinafter.

For another example, when the P-wave and the QRS complex have been successfully identified at the operation 606, if the identified P-wave is not before a corresponding identified QRS complex, it can be determined that an occurrence of supraventricular tachycardia is not likely, in which the P-wave and QRS complex condition for determining the supraventricular tachycardia condition is not met, and the process 600 can continues to use other criteria for detecting other cardiac conditions, or can go back to the operation 602. For example, a lagging P-wave can be associated with a potential uncommon AVNRT condition, and criteria for determining a potential uncommon AVNRT condition can be further compared to the P-wave and the QRS complex, details of which will not be further described hereinafter.

For another example, when the P-wave and the QRS complex have been successfully identified at the operation 606 with the identified P-wave before the corresponding identified QRS complex, if the identified QRS complex is narrower than a predetermined (e.g., regular) width, it can be determined that an occurrence of supraventricular tachycardia is not likely, in which the P-wave and QRS complex condition for determining the supraventricular tachycardia condition is not met, and the process 600 can continue to use other criteria for detecting other cardiac conditions, or can go back to the operation 602. For example, a narrow QRS complex can be associated with a potential AVNRT condition, and criteria for determining a potential AVNRT condition can be further compared to the P-wave and the QRS complex, details of which will not be further described hereinafter.

At operation 610, an ECG classifier (e.g., a binary ECG classifier) can be applied to determine a cardiac condition (e.g., an abnormality type) for the wearer. The ECG classifier can include a machine learning model trained in the above-described training process. The binary ECG classifier can determine whether a cardiac condition (e.g., a ventricular fibrillation condition or a supraventricular tachycardia condition) is occurring.

It should be noted that, besides the above-described example implementations, other implementations can be deduced without creative based on this disclosure. This disclosure is intended to cover any variation, use, or adaptation thereof, which are subject to the general principles of this disclosure and include common knowledge or technical means in the technical field.

The terms "comprise" or "include" or any other variant thereof are intended to encompass a non-exclusive inclusion, such that the processes, methods, articles, or apparatuses comprising a series of elements include not only the explicitly listed elements, but also other elements not explicitly listed, or elements that are inherent to such processes, methods, articles, or apparatuses. In the absence of more restrictions, the elements limited by the statement "including a . . . " do not exclude the presence of additional same elements in the processes, methods, apparatuses, or products.

It should be understood that although this disclosure uses the terms of "first, second, third," etc. for description, such description should not be limited to those terms. On the contrary, those terms are used only to distinguish the same type of information from each other. For example, without departing from the scope of this disclosure, the first information can also be referred to as the second information, and, similarly, the second information can also be referred to as the first information. Depending on the context, the words "if," as used herein can be interpreted as "when" or "while" or "in response to."

In addition, the articles "a" and "an" as used in this application and the appended claims should generally be construed to mean "one or more" unless specified otherwise or clear from context to be directed to a singular form. In the absence of more restrictions, the elements defined by the statement "including a . . . " do not preclude the existence of additional same elements in the processes, methods, articles, or devices that include the element.

While the disclosure has been described in connection with example implementations and embodiments, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method for processing electrocardiograph (ECG) data using a garment, comprising:
   receiving, by a communication interface, indication data transmitted by a user terminal, wherein the garment comprises the communication interface and the indication data comprises a current ECG monitor type;
   determining, by a processor, a current working lead from ECG leads formed in advance using flexible electrodes in the garment based on the current ECG monitor type; and
   receiving, by the processor through lead wires corresponding to the current working lead, ECG data collected by flexible electrodes corresponding to the current working lead.

2. The method of claim 1, further comprising:
   receiving, by a user interface, a first instruction triggered by a user, wherein the garment comprises the user interface, and the first instruction comprises the current ECG monitor type.

3. The method of claim 2, further comprising:
   receiving, by the user interface, a second instruction triggered by the user, wherein the second instruction comprises a time interval for the flexible electrodes corresponding to the current working lead; and
   based on the second instruction, receiving, by the processor in the time interval through the lead wires corresponding to the current working lead, the ECG data collected by the flexible electrodes corresponding to the current working lead.

4. The method of claim 2, further comprising:
   receiving, by the user interface, a third instruction triggered by the user; and
   based on the third instruction, transmitting, by the processor using a communication interface, the ECG data to at least one of a user terminal and a server, wherein the garment comprises the communication interface.

5. The method of claim 1, wherein the indication data is first indication data, the method further comprising:
   receiving, by the communication interface, second indication data transmitted by the user terminal, wherein the second indication data comprises a time interval for the flexible electrodes corresponding to the current working lead; and based on the second indication data, receiving, by the processor in the time interval through the lead wires corresponding to the current working lead, the ECG data collected by the flexible electrodes corresponding to the current working lead.

6. The method of claim 1, further comprising:
   transmitting, by the processor using the communication interface, the ECG data to at least one of the user terminal and a server.

7. The method of claim 1, further comprising:
   based on the ECG data, determining, by the processor, a health status for a wearer of the garment.

8. The method of claim 7, wherein determining the health status for the wearer of the garment comprises:
   determining whether the ECG data is in a target range associated with the wearer of the garment; and
   based on a determination that the ECG data is not in the target range, determining the health status for the wearer of the garment as abnormal, and generate an alert signal.

9. A wearable apparatus for processing electrocardiograph (ECG) data, comprising:
   at least two flexible electrodes, wherein the at least two flexible electrodes are capable of forming different leads based on predetermined configurations;
   at least two lead wires;
   an ECG data collector configured to receive ECG data collected by the at least two flexible electrodes, wherein each of the at least two flexible electrodes connects to the ECG data collector via at least one of the at least two lead wires;
   a processor connected to the ECG data collector for controlling the ECG data collector;
   a communication interface electrically connected with the processor configured to receive an instruction from a user, wherein the instruction comprises an ECG monitor type; and
   a user interface electrically connected to the ECG data collector and the processor, configured to receive the instruction from the communication interface, wherein the processor is configured to:
     determine a current working lead from the different leads for collecting the ECG data based on the ECG monitor type; and
     receive, through lead wires corresponding to the current working lead, the ECG data collected by flexible electrodes corresponding to the current working lead.

10. The wearable apparatus of claim 9, wherein the processor is further configured to:
    based on the instruction, determine a time interval for the flexible electrodes corresponding to the current working lead; and
    receive, in the time interval through the lead wires corresponding to the current working lead, the ECG data collected by the flexible electrodes corresponding to the current working lead.

11. The wearable apparatus of claim 9, wherein the processor is further configured to:
    based on the instruction, transmit, using the communication interface, the ECG data to at least one of a user terminal and a server.

12. The wearable apparatus of claim 9, wherein the processor is further configured to:
    transmit, using the communication interface, the ECG data to at least one of a user terminal and a server.

13. The wearable apparatus of claim 9, wherein the wearable apparatus comprises a garment.

14. A non-transitory computer-readable medium storing instructions which when executed by a computer system using a processor become operational with the processor for processing electrocardiograph (ECG) data using a garment, the non-transitory computer-readable medium comprising instructions to:
- receive, by a communication interface, indication data transmitted by a user terminal, wherein the garment comprises the communication interface and the indication data comprises a current ECG monitor type, wherein the current ECG monitor type is triggered by a user and received from a user interface;
- determine, by the processor, a current working lead from ECG leads formed in advance using flexible electrodes in the garment based on the current ECG monitor type;
- receive, by the processor through lead wires corresponding to the current working lead, ECG data collected by flexible electrodes corresponding to the current working lead; and
- based on the ECG data, determine a health status for a wearer of the garment.

15. The non-transitory computer-readable medium of claim 14, further comprising instructions to:
- transmit, by the processor using a communication interface, the ECG data to at least one of a user terminal and a server.

* * * * *